United States Patent [19]
Sonoyama et al.

[11] Patent Number: 5,134,077
[45] Date of Patent: * Jul. 28, 1992

[54] MICROORGANISMS OF THE GENUS ERWINIA USEFUL FOR PREPARING 2,5-DIKETO-D-GLUCONIC ACID

[75] Inventors: Takayasu Sonoyama; Shigeo Yagi; Bunji Kageyama, all of Osaka; Masahiro Tanimoto, Hyogo, all of Japan

[73] Assignee: Shionogi & Co., Ltd., Osaka, Japan

[*] Notice: The portion of the term of this patent subsequent to Nov. 7, 2006 has been disclaimed.

[21] Appl. No.: 403,298

[22] Filed: Sep. 5, 1989

Related U.S. Application Data

[60] Division of Ser. No. 243,215, Sep. 12, 1988, Pat. No. 4,879,229, which is a continuation of Ser. No. 925,538, Oct. 28, 1986, abandoned, which is a continuation of Ser. No. 288,332, Jul. 30, 1981, abandoned.

[30] Foreign Application Priority Data

Aug. 14, 1980 [JP] Japan ................... 55-112406

[51] Int. Cl.$^5$ .......................... C12R 1/18; C12P 7/60
[52] U.S. Cl. .................. 435/252.1; 435/137; 435/138; 435/847
[58] Field of Search ............. 435/137, 138, 847, 252.1

[56] References Cited

U.S. PATENT DOCUMENTS

| | | |
|---|---|---|
| 3,922,194 | 11/1975 | Sonoyama et al. |
| 3,959,076 | 5/1976 | Sonoyama et al. |
| 3,963,574 | 6/1976 | Sonoyama et al. |
| 3,998,697 | 12/1976 | Sonoyama et al. |
| 4,316,960 | 2/1982 | Kita et al. |
| 4,543,331 | 9/1985 | Sonoyama et al. |
| 4,879,229 | 11/1989 | Sonoyama et al. ........ 435/138 |

OTHER PUBLICATIONS

Wakisaka, Agr. Biol. Chem., vol. 28, No. 12, pp. 819–827 (1964).
American Type Culture Collection Data Sheet.
Letter from American Type Culture Collection dated Apr. 17, 1979 with attachments.
"Bergey's Manual of Determinative Bacteriology", 8th Ed., pp. 251–253, 332–339.
"The Prokaryotes-A Handbook on Habitats, Isolation, and Identification of Bacteria", vol. II, Chap. 102, pp. 1260–1271.
Wakisaka, "Agr. Biol. Chem.", vol. 28, No. 6, pp. 369–374 (1964).
White et al, "Journal of Applied Bacteriology", vol. 34, No. 2, pp. 459–475 (1971).
Suzuki et al, "Agricultural and Biological Chemistry", vol. 29, No. 5, pp. 456–461 (1965).
Breed et al, "Bergey's Manual of Determinative Bacteriology", 7th Ed., pp. 182–189; 349–359 (1957).
Carr, "Methods for Identifying Acetic Acid Bacteria", Academic Press, pp. 1–8 (1968).
Letter from American Type Culture Collection dated Mar. 6, 1979.

Primary Examiner—Herbert J. Lilling
Attorney, Agent, or Firm—Birch, Stewart, Kolasch & Birch

[57] ABSTRACT

2,5-Diketo-D-gluconic acid is prepared in high yield and in high broth concentration by cultivating newly isolated microorganisms of genus Erwinia in an aqueous nutrient medium in the presence of D-glucose. The production is also possible by simple contact of said microorganisms or their processed products therefrom, with D-glucose.

7 Claims, No Drawings ized microorganisms which belong to
MICROORGANISMS OF THE GENUS ERWINIA USEFUL FOR PREPARING 2,5-DIKETO-D-GLUCONIC ACID This application is a division of application Ser. No. 07/243,215 filed on Sep. 12, 1988, now U.S. Pat. No. 4,879,229, which is a continuation of application Ser. No. 06/925,538 filed on Oct. 28, 1986, now abandoned, which is a continuation of application Ser. No. 06/288,332 filed on Jul. 30, 1981, now abandoned.

BACKGROUND OF THE INVENTION

1. Field of the Invention

The present invention relates to a novel microbiological method for preparing 2,5-diketo-D-gluconic acid (hereinafter referred to as 2,5 DKG) from D-glucose. Particularly, it is concerned with a method for preparing 2,5-DKG by fermentation of new microorganisms which belong to Erwinia n. sps. or by simple contact of D-glucose with said microorganisms or their processed products, for instance, resting cells, immobilized cells, ground cells or any enzymes extracted therefrom, which may be suspended in a fluid medium or fixed on a surface of a stationary bed.

2. Description of the Prior Art 2,5 DKG is a useful intermediate in the production of L-ascorbic acid. Namely, 2,5 DKG can selectively and stereospecifically be reduced into 2-keto-L-gulonic acid, a precursor of L-ascorbic acid, in a promising new route for the latter product (See, for instance, U.S. Pat. Nos. 3,922,194, 3,959,076, 3,963,574 and 3,998,697).

In all of the known means, the production of 2,5 DKG has been achieved by cultivating aerobic microorganism strains which belong exclusively to genera Acetobacter, Acetomonas, Gluconobacter and Pseudomonas. No instance has hitherto been reported as to its production by means of cultivation using faculatatively anaerobic strains which belong to genus Erwinia.

SUMMARY OF THE INVENTION

It is therefore a primary object of the present invention to provide a method for preparing 2,5 DKG by the use of newly isolated microorganisms which belong to genus Erwinia.

It is still another object of the present invention to provide a method for preparing 2,5 DKG in a high yield and in a high broth concentration to facilitate a commercialization of the previously mentioned promising new route.

According to the present invention, there is provided a method for preparing 2,5 DKG characterized by contacting a 2,5 DKG producing microorganism of genus Erwinia or any processed products therefrom (any product obtained by treating cells of said microorganisms) with D-glucose.

The present invention may be embodied in a variety of modes, for instance, by cultivating at least one strain of said microorganisms in an aqueous nutrient medium containing D-glucose or by simply contacting said microorganisms or their processed products, i.e., resting cells, immobilized cells, or cell free enzymes extracted therefrom, with any substrate containing D-glucose.

Throughout this specification and claims, the term "cultivating" is used to include any modes of microbiological operations wherein the microorganisms are inoculated into and incubated in a medium to effect a fermentative action therein. The term "contacting" is used to mean operations wherein the microorganisms or any processed products therefrom are combined with the substrate to effect a conversion of D-glucose into 2,5 DKG, without regard to the length of the contact, i.e., incubation.

In the process of the present invention, any microorganisms of genus Erwinia can be utilized as far as the microorganisms are capable of selectively oxidizing D-glucose and converting it into 2,5 DKG. Examples of these strains, which have been isolated and determined to belong to new species of genus Erwinia by the present inventors, are collectively listed in Table 1 below. All of the listed strains, which have been deposited with the Fermentation Research Institute, Japan and with the American Type Culture Collection, Washington D.C., to be assigned FERM-P and ATCC numbers, respectively, are found to belong to the three new species and each constitutes variant with respect to the other within the species.

TABLE 1

| SHS- | Name given to the isolated microorganism | | FERM-P | ATCC |
|---|---|---|---|---|
| 2003 | Erwinia citreus | | 5449 | 31623 |
| 2006 | Erwinia punctata | | 5452 | 31626 |
| 2004 | " | var. | 5450 | 31624 |
| 2005 | " | var. | 5451 | 31625 |
| 2007 | " | var. | 5453 | 31627 |
| 2008 | Erwinia terreus | | 5454 | 31628 |
| 2009 | " | var. | 5455 | 31629 |
| 2010 | " | var. | 5456 | 31630 |
| 2011 | " | var. | 5457 | 31631 |

Details of taxonomic studies on these microorganisms will be collectively described in Table 2, below.

Table 2

A. Observations

1. Shape of Cells:

(Bouillon agar slants at 28° C. for 24, 72 and 168 hrs.) Cells predominantly single, rods of the listed dimensions with rounded ends in common with each of the observed strains. Sometimes, the presence of deformed cells of the indicated dimensions are observed in some strains.

| Strain: SHS- | Predominant cells: (Dimensions ($\mu$)) | Deformed cells: | | |
|---|---|---|---|---|
| | | Expanded cells: | Extended cells: (Dimensions ($\mu$)) | |
| 2003 | 0.8–1.2 × 1.0–2.9 | Observed | Observed, | 1.6 × 6.0–7.0 |
| 2004 | 1.0–1.5 × 1.5–3.3 | " | " | 0.7–0.8 × 4.0–5.0 |
| 2005 | 1.0–1.3 × 1.6–2.1 | " | " | 0.7–0.8 × 2.4–3.0 |
| 2006 | 1.1–1.3 × 1.3–1.9 | " | " | 0.6–0.8 × 2.4–2.7 |
| 2007 | 1.0–1.2 × 1.7–2.3 | None | None | — |
| 2008 | 0.8–0.9 × 1.5–1.7 | " | " | — |
| 2009 | 1.0 × 1.2–2.1 | " | " | — |
| 2010 | 1.0 × 1.0–2.0 | " | " | — |

-continued

| Strain: SHS- | Predominant cells: (Dimensions ($\mu$)) | Deformed cells: Expanded cells: | Extended cells: (Dimensions ($\mu$)) |
|---|---|---|---|
| 2011 | 1.1 × 1.3–2.0 | " | " | — |

2. Motility and Flagellation (Bouillon agar slants at 20° C. and 25° C. for 18 through 24 hrs.) Motility is confirmed by the hanging-drop method. Flagellation is confirmed under an optical microscope after being stained by Toda's method, or by means of transmission type electron microscope after being cultured in a sustained membrane culturing method. Strains SHS-2003, 2004, 2005, 2006 and 2007: Non-motile in common. Strain SHS-2008: Motile with mono-lateral flagellum. Strains SHS-2009, 2010 and 2011: Motile with one or two lateral flagella.

3. Spore: Not formed with each of the listed strains in common.

4. Gram straining: (Buillon agar slants at 28° C. for 24, 72 and 168 hrs.) Negative with each of the listed strains in common.

5. Acid fast: Negative in common.

B. Growth on a Variety of Media.

1. Bouillon agar colonies at 28° C. for 24, 48, 72 and 168 hrs. Initial colonies being circular, entire, smooth, translucent and butyrous in common.

| Strains SHS- | Brilliancy | Color | Progress of culture (Change in colonies, if any) |
|---|---|---|---|
| 2003 | Glistening | Pale reddish yellow | Convex. |
| 2004 | " | Pale beige | Smooth but gradually changes to rough. |
| 2005 | " | Pale beige | Convex but gradually changes to raised. |
| 2006 | " | Pale beige | Convex but gradually changes to umbonate. |
| 2007 | " | Pale beige | Raised but gradually changes to umbonate. |
| 2008 | Dull to glistening | Pale reddish yellow | Smooth but gradually changes to rough and convex. Dull but gradually changes to glistening. |
| 2009 | Glistening | Pale beige | Smooth but gradually changes to rough and raised. |
| 2010 | " | Pale beige | Convex but gradually changes to umbonate. |
| 2011 | " | Pale reddish yellow | Convex but gradually changes to flat. Viscid but gradually changes to butyrous. |

2. Bouillon agar slant at 28° C. for 24–168 hours. Initial colonies being filiform and butyrous in common.

| Strains SHS- | Growth | Brilliancy | Color | Progress of culture (change) |
|---|---|---|---|---|
| 2003 | Abundant | Glistening | Pale reddish yellow | — |
| 2004 | " | Dull to glistening | Pale beige | Dull but gradually changes to glistening. |
| 2005 | Moderate | Glistening | Pale beige | — |
| 2006 | " | Dull to glistening | Pale reddish yellow | Dull but gradually changes to glistening. |
| 2007 | Scanty | Dull | Pale reddish yellow | — |
| 2008 | Abundant | Dull to glistening | Pale reddish yellow | Dull but gradually changes to glistening. |
| 2009 | " | Dull to glistening | Pale reddish yellow | Dull but gradually changes to glistening. |
| 2010 | Moderate | Glistening | Pale reddish yellow | — |
| 2011 | " | " | Pale reddish yellow | — |

3. Bouillon broth at 28° C. for 24–168 hours. No odor in common.

| Strains SHS- | Growth on the surface of culture | | | Submerged growth | |
|---|---|---|---|---|---|
| | Ring along the tube wall | Membranous growth | Flocculent growth | Turbidity | Flocculent sediment |
| 2003 | On and after 3rd day | — | — | Slight | Scanty |
| 2004 | — | On 6th day | — | Slight to moderate | Initial compact sediment changes to scanty flocculant sediment |
| 2005 | — | " | — | Slight | Scanty |
| 2006 | — | " | — | Slight to moderate | " |
| 2007 | On 3rd day | On 7th day | — | Slight | " |
| 2008 | On 7th day | — | On 3rd day | " | " |
| 2009 | — | On 3rd to 6th day | On 7th day | " | " |
| 2010 | — | On 6th day | — | Slight to moderate | " |
| 2011 | — | On 4th day | — | Slight | " |

4. Bouillon gelatin stab at 20° C. for 40 days. No liquefaction in common. Growth along the stab line.

5. Litmus milk at 28° C. for 40 days. Strain SHS-2003: Acidification beings within 7 days. Weak and uniform coagulation begins on about the 18th day and is completed on the 38th day. From the 18th day to the 32nd day, the upper-layer becomes pink and the lower-layer becomes grayish brown, but on the 38th day, whole layer becomes pink in uniform. Strains SHS-2004, 2005, 2006, 2007, 2008, 2009, 2010 and 2011: No changes are observed throughout the incubation in common.

6. Potato slant at 28° C. for 24-168 hours. Filiform, butyrous and glistening in common.

| Strains | Growth | Color |
|---------|--------|-------|
| SHS-2003 | Abundant | Pale reddish yellow |
| 2004 | " | Beige |
| 2005 | Moderate | " |
| 2006 | " | Pale beige |
| 2007 | " | Beige |
| 2008 | Abundant | " |
| 2009 | " | " |
| 2010 | Moderate | " |
| 2011 | " | " |

C. Physiological Properties (Unless otherwise indicated, based on the results of the observation at 28° C. within 14 days)

1. Nitrite: Nitrite is produced from nitrate in common.

2. Nitrate respiration: Neither growth nor gas production is observed in paraffin-sealed bouillon broth containing 1% KNO$_3$ in common.

3. Methyl-red test: Positive in common, except strain SHS-2010 which is only very weakly positive.

4. Voges-Proskauer reaction (glucose): Strain SHS-2003: Very weakly positive. Strains SHS-2004, 2005, 2007, 2008, 2010 and 2011: Positive. Strains SHS-2006 and 2009: Negative or very weakly positive.

5. Indole: Negative in common.

6. Hydrogen sulfide:
 (i) Bacto peptone water-lead acetate paper: Positive in common.
 (ii) TSI agar: Negative in common.
 (iii) Kliegler agar: Negative in common.

7. Ammonia: Not produced in common.

8. Hydrolysis of starch: Negative in common.

9. Growth on citrate media:
 (i) Simmon's medium*: Growth in common.
 (ii) Christensin's medium: Growth in common.
*Supplemented with a vitamine mixture.

10. Growth with inorganic nitrogen sources:
 (i) Ammonium (Glucose-Hucker's medium)*: Growth in common.
 (ii) Nitrate (Glucose-Dimmick's medium)*: Growth is observed for Strains SHS-2003, 2004, 2005, 2008, 2009, 2010 and 2011: while SHS-2006 does not grow and SHS-2007 only grows very weakly.
*Supplemented with a vitamine mixture.

11. Pigment (Plate straeia culture):
 (i) Blue pigment (Yeast extract 1%, glucose 1%, CaCO$_3$ 2%, at 28° C. for 7 days): Negative in common.
 (ii) Pink diffusible pigment (the same medium as above): Negative in common.
 (iii) Yellow pigment (bouillon agar at 28° C. for 7 days): Negative in common.

12. Urease: Negative in common.

13. Catalase: Positive in common.

14. Oxidase (bouillon agar slant, for 18-24 hours, containing tetramethylphenylenediamine): Negative in common.

15. Temperature relations (Bacto yeast extract 0.5%, Bacto peptone 0.5% and glucose 0.5%, pH 7):

| Strains SHS- | Temp. of growth (°C.) | Optimum temp. of growth (°C.) |
|--------------|----------------------|------------------------------|
| 2003 | 8.5-38.5 | 18-31 |
| 2004 | 6.5-40.0 | 20-34 |
| 2005 | 6.5-38.5 | 22-28 |
| 2006 | 6.5-38.5 | 21-28 |
| 2007 | 4.0-47.5 | 21-27 |
| 2008 | 18.0-40.0 | 19.5-32.5 |
| 2009 | 8.5-38.5 | 24-30 |
| 2010 | 6.5-40.0 | 20-34 |
| 2011 | 4.0-40.0 | 19.5-24 |

16. pH relations (glycerol 1%, Bacto yeast extract 0.05%, Bacto peptone 1%, NaCl 0.5%, in 0.1M 3,3-dimethylglutaric acid buffer, 28° C. for 2-4 days)

| Strains SHS- | pH of growth | Optimum pH of growth |
|--------------|--------------|---------------------|
| 2003 | 5.5-8.0 | 6.0-7.5 |
| 2004 | 5.5-8.5 | 6.0-7.5 |
| 2005 | 5.5-8.5 | 6.0-7.5 |
| 2006 | 5.5-8.5 | 6.0-7.5 |
| 2007 | 5.5-8.5 | 6.0-7.5 |
| 2008 | 5.5-7.5 | 6.0-7.5 |
| 2009 | 5.5-8.0 | 6.0-7.5 |
| 2010 | 6.0-8.0 | 6.0-7.5 |
| 2011 | 5.5-7.5 | 6.0-7.5 |

17. Oxygen requirement: Facultatively anaerobic in common.
 (i) Liquid paraffin sealed stab culture: (Glucose-BCP medium, containing Bacto beef extract 1%, Bacto peptone 1%, Bacto yeast extract 0.2%, NaCl 0.5%, bromocresol purple 0.004% and agar powder 1.5%, pH adjusted at 7.0-7.2, was dispensed in test tubes of 18 mm in diameter in a depth of about 8 cm. The dispensed medium was sterilized at 121° C. for 15 min. . Stab inoculation was performed before complete solidification of the medium. The test tubes were then sealed with sterile liquid paraffin (5-7 ml) in 4 cm depth.) Tubes were cultured at 28° C. and observed over a period of 7 days.

There is observed a distinct growth along the stab line from the top to the bottom of the medium within 2-3 days and the culture begins to become slightly yellowish uniformly to show a distinct difference in color from the sealed cultured tube of the non-inoculated control with each of the listed strains. The degree of yellow color further increases with the lapse of time.

(ii) Gas-Pak anaerobic system (BBL): (Bacto nutrient agar plate, containing Bacto beef extract 1%, Bacto peptone 1%, NaCl 0.5% and agar powder 1.5%, or GYP agar plate, containing glycerol 0.5%, Bacto yeast extract 0.5%, Bacto peptone 0.3%, KH$_2$PO$_4$ 0.1%, MgSO$_4$.7H$_2$O 0.02% and agar powder 1.5%, pH adjusted at 7.0-7.2). Slight streak inoculation of a suspension of the test organism was cultured at 28° C. for 48 hrs. after the oxygen was removed by two hour's reaction at 45° C. in an incubator.

Only weak growth is observed in common. The growth is weaker than that of Escherichia coli used as control.

18. O-F test (Hugh-Leifson's method): Fermentative in common. Medium containing Bacto trypton 1%, Bacto yeast extract 0.1%, bromocresol purple 0.004%, glucose (or lactose) 1% and agar powder 0.2%, pH adjusted at 7.0–7.2 was dispensed to test tubes (18 mm in diameter) in depth of about 8 cm. Dispensed medium was sterilized at 121° C. for 15 min.. After the temperature of the medium became about 30°–40° C., duplicate inoculations were performed for each organism of the listed strains, and one tube of each pair was then sealed with sterile liquid paraffin (5–7 ml) about 4 cm in depth. Tubes were cultured at 28° C. and observed over a period of 7 days.

Acid is produced under both aerobic and anaerobic conditions from D-glucose (also from lactose, in the case of SHS-2003), but no gas. A distinct growth along the stab line from the top to the bottom is observed with the sealed culture in as the non-sealed culture.

Anaerobical acid formation is not so rapid as Escherichia coli used as control.

19. Production of acids and gases from carbohydrates: (Modified Barsikow's method at 28° C. for 7 days, stationary)

(i) L-glutamic acid: Negative with SHS-2003, 2008, 2009, 2010 and 2011. Positive with SHS-2004, 2005, 2006 and 2007.
(ii) L-lysine: Negative in common.
(iii) L-arginine: Negative in common.
(iv) L-ornithine: Negative in common.

25. Lipase (Modified Starr's method, Starr, M.P., Science, 93, 333–334 (1941)): Negative in common.

26. D-gluconate oxidation (Shaw, C & Clarke, P.H., J. Gen. Microbiol., 13, 155–161 (1955)): Positive in common.

27. Pectate degradation (A. M. Paton, Nature, 183, 1812–1813 (1959)): Negative in common.

28. Casein hydrolysis (D. W. Dye, N.Z. J. Sci., 11, 590–607 (1968)): Negative in common.

29. Symplasmata (Graham, D. C. & Hodgkiss, W., J. Appl. Bacteriol., 30(1), 175–189 (1967)): Negative with SHS-2003, 2004, 2005, 2007, 2008 and 2009 Positive with SHS-2006, 2010 and 2011.

30. DNase (Bacto DNase Test Agar): Negative in common.

| Strains SHS- | Fructose | Glucose | Galactose | β-Methyl-glucoside | Mannose | Ribose | Mannitol | Salicin | Xylose | Lactose |
|---|---|---|---|---|---|---|---|---|---|---|
| 2003 | + | + | + | + | + | + | + | + | + | + |
| 2004 | + | + | + | + | + | + | − | + | + | − |
| 2005 | + | + | + | + | + | + | − | + | + | − |
| 2006 | + | + | + | + | + | + | − | + | + | − |
| 2007 | + | + | + | + | + | + | − | + | + | − |
| 2008 | + | + | + | + | + | + | − | + | + | − |
| 2009 | + | + | + | + | + | − | − | + | + | − |
| 2010 | + | + | + | + | + | ± | − | + | + | − |
| 2011 | + | + | + | + | + | − | − | + | + | − |

| Strains SHS- | Melibiose | Cellobiose | Glycerol | Sucrose | Maltose | Dextrin | Esuclin | Rhamnose | Sorbitol |
|---|---|---|---|---|---|---|---|---|---|
| 2003 | + | + | + | − | − | − | − | − | − |
| 2004 | + | − | + | + | − | − | − | − | − |
| 2005 | + | + | + | + | − | − | − | − | − |
| 2006 | + | + | − | + | − | − | − | − | − |
| 2007 | + | + | − | + | − | − | − | − | − |
| 2008 | + | + | + | + | − | − | − | − | − |
| 2009 | + | + | + | + | − | − | − | − | − |
| 2010 | + | + | − | + | − | − | − | − | − |
| 2011 | + | + | − | + | − | − | − | − | − |

| Strains SHS- | Raffinose | Adonitol | Dulcitol | Melezitose | Arabinose | α-Methyl-glucoside | Inositol |
|---|---|---|---|---|---|---|---|
| 2003 | − | − | − | − | − | − | − |
| 2004 | − | − | − | − | − | − | − |
| 2005 | ± | − | − | − | − | − | − |
| 2006 | − | − | − | − | − | − | − |
| 2007 | + | − | − | − | − | − | − |
| 2008 | − | − | − | − | − | − | − |
| 2009 | − | − | − | − | − | − | − |
| 2010 | − | − | − | − | − | − | − |
| 2011 | − | − | − | − | − | − | − |

Note:
(i) Acid but no gas, produced (+)
(ii) Slight acid but no gas, produced (±)
(iii) Neither acid nor gas, produced (−)

20. Methylene blue (bouillon broth, 18–24 hrs.): Reduced in common.
21. D-Gluconic acid: Utilized in common.
22. 2-Keto-D-gluconic acid: Utilized in common.
23. Production of reduced compound from sucrose (Bergey's manual of determinative bacteriology 8th Ed. (1974) page 335, Table 8.19, foot note f): Positive in common except for SHS-2003.
24. Decarboxylation of various amino acids: (Shaw, C & Clarke, P.H., J. Gen. Microbiol., 13, 155–161 (1955))

31. Phenylalanine deaminase (Phenylalanine/Malonic acid medium, available from Nissui Pharmaceutical Co. Ltd.): Strains SHS-2003, 2008, 2009, 2010 and 2011: Negative or very weakly positive. Strains SHS-2004, 2005, 2006 and 2007: Negative.

32. KCN inhibition: Positive in common.

33. Growth in 5% NaCl bouillon: Positive in common.

34. Auxotrophy (Gray & Tatum's medium): Requires nicotinic acid or nicontinamide in common.

35. Utilization of some organic compounds (D. W. Dye, N.Z. J. Sci., 11, 590–607 (1968), OY medium, 28° C., 20 & 44 hrs, shaking):

| Strains SHS- | Ace-tate | Ci-trate | For-mate | Fuma-rate | Gluco-nate | Mal-ate | Succi-nate | Ben-zoate |
|---|---|---|---|---|---|---|---|---|
| 2003 | + | + | + | + | + | + | + | − |
| 2004 | ± | + | + | + | + | + | + | − |
| 2005 | ± | + | + | + | + | + | + | − |
| 2006 | ± | + | + | + | + | + | + | − |
| 2007 | ± | + | + | + | + | + | + | − |
| 2008 | + | + | + | + | + | + | + | − |
| 2009 | + | + | + | + | + | + | + | − |
| 2010 | + | + | + | + | + | + | + | − |
| 2011 | + | + | + | + | + | + | + | − |

| Strains SHS- | Galaturo-nate | Malo-nate | Oxa-late | Propio-nate | Tarta-rate | Lac-tate |
|---|---|---|---|---|---|---|
| 2003 | − | − | − | − | − | + |
| 2004 | − | − | − | − | − | ± |
| 2005 | − | − | − | − | − | ± |
| 2006 | − | − | − | − | − | ± |
| 2007 | − | − | − | − | − | ± |
| 2008 | − | − | − | − | − | + |
| 2009 | − | − | − | − | − | + |
| 2010 | − | − | − | − | − | + |
| 2011 | − | − | − | − | − | + |

Note:
(i) Utilizes as a single carbon source (+)
(ii) Slightly utilizes or does not utilize as a single carbon source (±)
(iii) Does not utilize (−)

36. Ubiquinone (Y. Yamada, K. Aida & T. Uemura, J. Gen. Appl. Microbiol., 15, 181–196 (1969)): Strains SHS-2003, 2008: Ubiquinone-8 (and Ubiquinone-7) Strains SHS-2004, 2005, 2006, 2007, 2009, 2010 and 2011: Ubiquinone-8.

D. Origin

Strains SHS-2003, 2004, 2006, 2007, 2010 and 2011: Mandarin orange.

Strains SHS-2005 and 2009: Persimmon.

Strains SHS-2008: Soil.

The strains listed in Table 1 were determined by comparing the above-mentioned taxonomical properties of the respective strains in Table 2, with the descriptions in the Bergey's Manual of Determinative Bacteriology 8th Ed. 1974 (hereinafter, will be simply referred to as "Manual") to lead the conclusion which will be described below.

1) Allocation in terms of Family:

On the basis of the above described results of the observation that all of the listed strains are short rods of gram-negative and facultatively anaerobic, which form no spores and show a catalase activity but no oxidase activity, they are determined to belong to Family Enterobacteriaceae.

2) Allocation in terms of Genus:

All of the listed strains are determined to belong to Genus Erwinia on the basis of the taxonomical properties, particularly on those of, the productions of acids from β-methylglucoside and sucrose (except for SHS-2003 which does not produce acid from sucrose but utilizes the same as a sole carbon source) but not from adonitol, dulcitol or melezitose; no utilization of benzoate, oxalate and propionate; being incapable of hydrolysing starch; being incapable of decarboxylating glutamic acid, arginine, lysine and ortinine (except for SHS-2004, 2005, 2006 and 2007 which decarboxylate glutamic acid) and showing no urease or lipase activity.

3) Allocation in term of species:

Strain SHS-2003:

Although this strain is considered to be closely related to *Erwinia stewartii* of group herbicola defined in the Manual on the basic of no flagellation, it still has other taxonomical properties greatly different from those of *Erwinia stewartii* in the following points:

(i) Requirement of nicotinic acid or nicotinamide for growth, (ii) Production of hydrogen sulfide from cysteine, (iii) Reduction of nitrate to nitrite, (iv) No acid production from sucrose*, arabinose, raffinose or sorbitol, (v) Production of acids from salicin, cellobiose and glycerol, and (vi) No utilization of tartarate as a sole carbon source.
(*Though it cannot produce acid from sucrose, it can utilize the same as a sole carbon source)

Furthermore, since this strain did not show a coincidence with any other known species in the genus defined in the Manual, it was concluded that it should be allocated to a new species, named as *Erwinia citreus* by the present inventors.

Strains SHS-2004, 2005, 2006 and 2007:

Although these strains are likewise considered to be closely related to *Erwinia stewartii* in view of no flagellation, they still share other common taxonomical properties greatly different from those of *Erwinia stewartii* in the following points:

(i) Requirement of nicotinic acid of nicotinamide for growth.

(ii) Production of hydrogen sulfide from cysteine, (iii) Reduction of nitrate to nitrite, (iv) Decarboxylation of gultamic acid, (v) No acid production from arabinose, mannitol, lactose or sorbitol, (vi) Production of acids from salicin and cellobiose, and (vii) No utilization of tartarate as a sole carbon source.

Furthermore, these strains are observed to be different from the previously described strain SHS-2003 in the points; decarboxylation of glutamic acid; being scarcely capable of utilizing lactose, acetate and lactate as sole carbon source; being unable to produce acids from mannitol and lactose; and having no activity on litmus milk.

Moreover, since these strains did not show coincidences with any other known species in the genus defined in the Manual, it was concluded that they should be allocated to a new species, named as *Erwinia punctata* by the present inventors.

Of these strains, the strains SHS-2004 and 2006 are common in their taxonomical properties in the points;

(i) No acid production from raffinose, and (ii) No utilization of mannitol, acetate or lactate.

However, SHS-2004 differs from SHS-2006 in the points:

(i) Production of acetoin from glucose, (ii) Utilization of nitrate as nitrogen source, (iii) Production of acid from glycerol, and (iv) Utilization of formate as a sole carbon source.

On the other hand, the strain SHS-2005 has the same taxonomical properties as those of SHS-2006 in the point of being scarcely capable of utilizing mannitol, acetate and lactate as their sole carbon source, but the former differs from the latter in the points:

(i) Production of acid from glycerol, (ii) Production of acetoin from glucose, (iii) Formation of fluorescent pigments in King B medium, (iv) Scarce production of acid from raffinose, and (v) Utilization of formate as a sole carbon source.

Furthermore, the strain SHS-2007 likewise has the properties as those of SHS-2006 in the points of being scarcely capable of utilizing mannitol, acetate and lactate as their sole carbon sources, but the former differs from the latter in the points:

(i) Production of acid from reffinose, (ii) Production of acetoin from glucose, (ii) Utilization of formate as a sole carbon source, and (iv) Wide temperature range for growth such as 4.0°-47.5° C.

On the basis of the above indicated results of observation, all of the strains SHS-2004, 2005, 2006 and 2007 are likewise found to belong to said *Erwinia punctata* and each forms a variant with respect to the others.

Strains SHS-2008 and 2010:

Although these strains are considered to be closely related to *Erwinia tracheiphila* or *Erwinia quercina* in view of their motility with mono-lateral flagellum, the taxonomical properties of them are still greatly different from those of *Erwinia tracheiphila* defined in the Manual, in the following points:

(i) Growth at a temperature higher than 36° C., (ii) Abundant growth on bouillon agar media, (iii) Showing mucoid growth, (iv) Reduction of nitrate to nitrite, (v) Production of acids from salicin, xylose, melibiose and mannose, and (vi) Utilization of lactate as a sole carbon source.

On the other hand, there are differences in their taxonomical properties from those of *Erwinia quercina* defined in the Manual in the following points:

(i) Oxidation of gluconic acid, (ii) Reduction of nitrate to nitrite, (iii) Production of acids from melibiose and cellobiose, (iv) No acid production from mannitol, α-methylglucoside, esuclin and sorbitol, and (v) No gas production on glucose-peptone media.

Moreover, since these strains do not show coincidences with any other known species in the genus defined in the Manual, they were found to be suitably allocated to a new species, named as *Erwina terreus* by the present inventors.

Furthermore, the strain SHS-2010 shows substantial coincidence with SHS-2008, except for certain differences observed in the following points:

(i) No acid production from glycerol, (ii) Production of acid from ribose by SHS-2008 in contrast to very scarce production by SHS-2010, (iii) Slightly positive in methyl red test, and (iv) Formation of fluorescent pigments on King B medium.

Strain SHS-2009:

This strain is considered to be closely related to *Erwinia tracheiphila, E. quercina* and *E. herbicola*, var. *herbicola* in view of motility with mono-lateral flagellum.

However, there is remarkable differences in the taxonomical properties of this strain as compared with those of *Erwina tracheiphila* defined in the Manual in the following points:

(i) Abundant growth in bouillon agar media, (ii) Growth at a temperature higher than 36° C.

(iii) Showing mucoid growth.

(iv) Reduction of nitrate to nitrite, and (V) Production of acids from salicin, xylose, melibiose cellobiose, glycerol and mannose.

In addition to this, there is also found remarkable differences from those of *Erwinia quercina*, in the following points:

(i) Oxidation of gluconate, (ii) Reduction of nitrate to nitrite, (iii) Weak formation of acetoin from glucose, (iv) Production of acids from xylose, melibiose and cellobiose, (v) No acid production from mannitol, α-methylglucoside, esuclin, ribose or sorbitol, (vi) No utilization of tartarate as a sole carbon source, and (vii) No gas production from glucose-peptone medium.

Furthermore, there is still found remarkable differences in the properties of SHS-2010 from those of *Erwinia herbicola*. var. *herbicola* in the following points:

(i) Requirement of nicotinic acid or nicotinamide for the growth, (ii) Weak formation of acetoin from glucose, (iii) No liquefaction of gelatin, (iv) Production of acids from melibiose, cellobiose and glycerol, and (v) No acid production from arabinose, mannitol, maltose, dextrine, rhamnose, ribose or sorbitol.

Although some differences are still remaining in comparing this strain with the aforedefined SHS-2008, in the points:

(i) Weak acetoin formation from glucose, and (ii) No acid production from ribose, the former coincides with the latter in the other dominating properties and thus identified to be a variant of the afore-defined *Erwinia terreus*.

Strain SHS-2011:

This strain is considered to be closely related to *Erwinia tracheiphila* or *Erwinia amylovora* in view of its motility with a mono-lateral flagellum.

When the properties of this strain are first compared with those of *Erwinia tracheiphila* defined in the Manual, there is recognized remarkable differences in the following points;

(i) Moderate growth in bouillon agar media, (ii) Growth at a temperature higher than 36° C.

(iii) Showing mucoid growth, (iv) Reduction of nitrate to nitrite, (v) Production of acids from salicin, xylose, melibiose, cellobiose and mannose, and (vi) Utilization of lactate as a sole carbon source.

When they are compared with those of *Erwinia amylovola*, there is recognized remarkable differences in the following points:

(i) Formation of hydrogen sulfide from cysteine, (ii) Growth at a temperature as high as 36° C., or higher, (iii) Reduction of nitrate to nitrite, (iv) No liquefaction of gelatin, (v) Production of acids from salicin, xylose, melibiose, cellobiose and mannose, and (vi) No acid production from ribose.

On the other hand, when this strain is compared with the SHS-2008, it is recognized to be in a coincidence with the latter in the properties except for no production of acid from ribose or glycerol, and is identified as a variant of the aforedefined *Erwinia terreus*.

In addition to those isolated microorganisms (wild strains), any spontaneous mutants obtained therefrom may likewise be utilized in the method of this invention with advantages as far as they are capable of producing 2,5-diketo-D-gluconic acid, and it is needless to say that any strains, obtained by artificially or inductively mutating or modifying these isolated microorganisms so that they exhibit desired properties, may likewise be utilized in embodying the present invention in a smooth way by suitably taming the strains.

The aforedefined microorganisms grow abundantly in an aqueous nutrient medium containing D-glucose, as a main carbon source, corn steep liquor as a nitrogen source and a small amount of inorganic salts. If they are aerobically cultured, they grow on media of very-high D-glucose concentration with sufficient stability to produce 2,5-diketo-D-gluconic acid (2.5 DKG) in good yield, as compared with the known microorganisms which have been used in producing the same product.

The concentration of D-glucose in the broth may be as high as 40 w/v % if particularly desired so, though it is usually convenient for an economical production of 2,5-diketo-D-gulconic acid to maintain this concentration to a range of 15-25 w/v % and more preferably, to approximately 20 w/v %.

The temperature of fermentation broth may be in a range of 15°–35° C., preferably, in that of 20°–30° C. and more preferably at approximately 28° C. An initial pH value of the medium may be in a range of 5.5-7.5 and preferably in that of 6.0-7.0.

The pH value of the broth may be maintained at a desired range of 4.0-5.5 during the fermentation by incorporating suitable inorganic salts having a buffering action in the starting broth, or by consecutively feeding suitable bases into the broth with the progress of the fermentation. The salt can be exemplified by calcium carbonate and the base can be exemplified by sodium hydroxide.

The inoculated fermentation broth is stirred constantly with agitator (Ca. 1,740 r.p.m.) under aeration at a ratio of about 600N nl/min..

The fermentation completes when the convrsion of D-gulcose into 2,5 DKG reaches a value which corresponds to about 90% yield of the latter, which time is about 17-31 hours after beginning cultivation.

The accumulated 2,5 DKG or its salts may be isolated as crystals from the fermenation broth after being treated with any means such as pH adjustment, or alternatively, the broth may advantageously be utilized as such for the nutrient medium of the next stage. For instance, the broth containing 2,5 DKG may directly be utilized for the production of 2-keto-L-gulonic acid, thus the latter can be obtained in high yield in a simple procedure as compared with the conventional method.

In addition to the previously described fermentation, the present invention may be embodied by simply contacting any processed products of the microorganism with any substrates containing D-glucose. In these cases, conditions similar to those described above in connection with the cultivation of viable cells may also be applied to the incubation of the processed products in the substrate, and the conversion starts immediately after the starting of contact.

DESCRIPTION OF THE PREFERRED EMBODIMENTS

In the following description, the present invention will be elucidated in more detail by way of examples.

Example 1

(1) Seed medium:
An aqueous solution containing;
D-glucose (hydrated, content 91%): 1.0 wv %,
Corn Steep Liquor (CSL): 5.0 w/v %,
Potassium bihydrogen phosphate ($KH_2PO_4$): 0.1 w/v %,
Magnesium sulfate ($MgSO_4 \cdot 7H_2O$): 0.02 w/v %, and
Calcium carbonate ($CaCO_3$): 0.5 w/v %
is adjusted to pH 6.8–7.0 with 10% aqueous solution of NaOH, divided into 50 ml portions and placed in sterilized 500 ml conical flasks to give the seed media.

(2) Seed culture:
Each of said media in the flasks is inoculated with one loopful of the strains listed in Table 3 below and shaken (stroke: 71 mm, 270 s.p.m.) at 28° C. for about 8 hours. The culture is terminated when the optical density (O.D.) of the media becomes approximately 8 (end point).

(3) Fermentation broth:
An aqueous solution containing;
D-glucose: 20.0 w/v %,
CSL: 3.0 w/v %,
$KH_2PO_4$: 0.1 w/v % and
$CaCO_3$: 6.3 w/v %
is adjusted to pH 6.8-7.0, divided into 455 ml portions and placed in 1 L fermentors to give the fermentation broth, into which each 45 ml of said seed media is added.

(4) Fermentation:
The fermentation is carried out under the conditions of:
Temperature: 28° C.
Stirring: 1740 r.p.m.
Aeration: 600N ml/minute
Time: 17-31 hours (5) Determination:
The product is chromatographed on a filter paper carrier by ascending under the conditions specified below, and the spots are quantitatively determined by densitometry.
(i) Carrier: Toyo Roshi No. 50
(ii) Developing solvent: Phenol: Formic acid: Water = 75:4:25
(iii) staining: Spraying of AHF solution (a solution of water-saturated n-butanol (100 ml) containing anilin (0.93 g) and phthalic acid (1.66 g) followed by a color-developing treatment at 105° C. for 2 minutes.
(iv) Color and Rf value:

| Substance: | Color: | Rf: |
| --- | --- | --- |
| 2,5-diketo-D-gluconic acid | Brown | 0.16–0.18 |
| 2-keto-D-gluconic acid | Pink | 0.27–0.29 |
| D-glucose | Brown | 0.48–0.50 |

In addition to this, a thin layer chromatography is also performed with "TLC alumisheet cellulose" (tradename of E Merck A. G.) and the same developing solvent system and straining operation as described above. In this case, the determination is performed by comparison of the chromatogram with that obtained with an authentic specimen.

(6) Termination:

The fermentation is terminated at a time when the pink spot of 2-keto-D-gluconic acid disappears from said paper or thin layer chromatogram.

(7) Results:

TABLE 3

| Strains SHS- | Seed Culture At termination | | | Fermentation Culture | | | 2,5-diketo-D-gluconic acid. | |
|---|---|---|---|---|---|---|---|---|
| | pH | OD | Time (hrs.) | At termination | | Time (hrs.) | Conc. (w/v %) | Yield for D-glucose (%) |
| | | | | pH | OD | | | |
| 2003 | 7.0 | 10.0 | 8 | 5.4 | 12.3 | 18 | 19 | 88 |
| 2004 | 6.0 | 8.5 | 8 | 4.9 | 12.0 | 17 | 19 | 89 |
| 2005 | 6.9 | 9.5 | 9 | 5.1 | 12.6 | 20 | 19 | 86 |
| 2006 | 5.9 | 7.5 | 8 | 4.7 | 12.0 | 21 | 19 | 89 |
| 2007 | 6.0 | 7.0 | 8 | 4.9 | 12.6 | 17 | 19 | 89 |
| 2008 | 5.6 | 3.1 | 10 | 5.3 | 12.4 | 29 | 17 | 70 |
| 2009 | 5.8 | 3.4 | 10 | 5.7 | 12.4 | 21 | 18 | 79 |
| 2010 | 5.4 | 2.5 | 10 | 5.4 | 12.8 | 31 | 18 | 75 |
| 2011 | 5.3 | 2.4 | 10 | 5.1 | 12.2 | 31 | 17 | 75 |

Examples 2 and 3

Production with Cell Suspension and with Crude Enzyme Extract (1) Medium used for obtaining microoganism cells:
An aqueous solution containing;
Yeast extract (available from Daigo Eiyo Yakuhin K.K.): 0.1 w/v %
$KH_2PO_4$: 0.1 w/v %
$NaSO_4 \cdot 7H_2O$: 0.02 w/v % and
$CaCO_3$: 0.6 w/v %
is adjusted to pH 7.0, divided into 80 ml portions, and placed in conical flasks (500 ml).

(2) Cultures for collecting micoorganism cells and for separating crude enzyme extract:

Each of said media is inoculated with the strains listed in Table 4 below in a similar manner as described in the seed culture of Example 1 and shaken (stroke, 71 mm, 270 s.p.m.) at 28° C. for 16 hours.

After the shaking, the microorganism cells are collected by centrifuging the cultured media, washed twice with saline and divided into two portions.

One of said portions is suspended again in saline to give the cell suspension. The other is suspended in a 1/50M tris-HCl buffer (pH 7.5) wherein the cells are disruptured by ultra-sonic treatment and centrifuged to remove insoluble residue therefrom in order to obtain crude cell-free enzyme extract as its supernatant.

(3) Incubation with cell suspension:

A mixture is prepared with 1/10M 3,3-dimethylgultaric acid buffer (pH 5.0) containing about 5 w/v % of D-glucose, wherein the cell concentration is adjusted so that the O.D. at 660 mμ is approximately 10. The mixture is divided into 10 ml portions, placed in test tubes of 23 mm (diameter)×196 mm (length) and incubated at 28° C. for 3 hours.

The mixture is centrifuged to give a supernatant which is analyzed by paper chromatography. The results are summarized in Table 4 below, wherein the concentrations of D-glucose in the mixture before incubation are also given.

TABLE 4

| | (Concentrations after 3 hours shaking) | | |
|---|---|---|---|
| Strains SHS- | D-glucose (%) before incubation | 2-keto-D-gluconic acid (%) | 2,5-diketo-D-gluconic acid (%) |
| 2003 | 4.9 | 2.7 | 0.8 | 1.9 |
| 2004 | 5.0 | 1.9 | 0.7 | 1.5 |
| 2005 | 5.0 | 2.6 | 0.6 | 0.7 |
| 2006 | 5.0 | 1.9 | 0.9 | 1.1 |
| 2007 | 5.0 | 1.4 | 0.3 | 1.4 |
| 2008 | 5.0 | 1.3 | 0.8 | 1.2 |
| 2009 | 5.2 | 1.9 | 0.7 | 1.3 |
| 2010 | 5.0 | 2.9 | 0.5 | 0.9 |
| 2011 | 5.0 | 2.8 | 0.7 | 0.9 |

(4) Incubation with crude enzyme extract:

To a mixture prepared in a similar manner as described in (3) above, the crude enzyme extract is added so that its concentration is 0.25 mg/ml, determined as a protein quantity (Folin's method). After being shaken as previously described, the mixture is treated with two drops of 10 w/v % trichloroacetic acid solution to remove the protein portion, and chromatographed on a filter paper. The results are shown in Table 5 below.

TABLE 5

| Strain SHS- | (Concentrations after 3 hours shaking) | |
|---|---|---|
| | 2-keto-D-gluconic acid (%) | 2,5-diketo-D-gluconic acid (%) |
| 2003 | 1.0 | 1.0 |
| 2004 | 0.6 | 0.8 |
| 2005 | 0.4 | 0.4 |
| 2006 | 0.5 | 0.5 |
| 2007 | 0.3 | 0.4 |
| 2008 | 0.8 | 0.5 |
| 2009 | 0.4 | 0.6 |
| 2010 | 0.3 | 0.3 |
| 2011 | 0.3 | 0.3 |

What is claimed is:

1. A substantially biologically pure culture consisting essentially of a microorganism selected from the group consisting of Erwinia citreus, Erwinia punctata and Erwinia terreus which produces a recoverable quantity of 2,5-diketo-D-gluconic acid of a salt thereof upon cultivation in the presence of D-glucose and has the follwing characteristics in common:

(1) negative gram staining,
(2) negative in acid fastness,
(3) initial colonies are circular, entire, smooth, translucent and butyrous when grown in bouillon agar colonies at 28° C. for 24, 48, 72 and 168 hours,
(4) filiform, butyrous and glistening in potato slant at 28° C. for 24–168 hours,
(5) nitrite is produced from nitrate,
(6) neither growth nor gas production is observed in paraffin-sealed bouillon broth containing 1% $KNO_3$,
(7) positive to weakly positive in a methyl red test,
(8) negative to indole,
(9) ammonia not produced,
(10) does not hydrolyze starch,
(11) grows on citrate media,
(12) negative to blue pigment, pink diffusible pigment or yellow pigment,
(13) positive to catalase,
(14) negative to oxidase,
(15) does not grow effectively at a termperature above 47.5° C.,
(16) facultatively anaerobic with regard to oxygen,

(17) fermentative in the Hugh-Leifson's method,
(18) incapable of producing acid or gas from esculin, rhamnose or sorbitol,
(19) reduces methylene blue,
(20) no decarboxylation of L-lysine, L-arginine or L-ornithine,
(21) negative to lipase,
(22) positive to D-gluconate oxidation,
(23) negative to pectate degradation,
(24) negative to casein hydrolysis,
(25) negative to DNase,
(26) positive to KCN inhibition,
(27) positive to growth in 5% NaCl, and
(28) requires nicotinic acid or nicotinamide for auxotrophy.

2. A substantially biologically pure culture according to claim 1, wherein said microorganism is *Erwinia citreus*.

3. A substantially biologically pure culture according to claim 1, wherein said microorganism is *Erwinia punctata*.

4. A substantially biologically pure culture according to claim 1, wherein said microorganism is *Erwinia terreus*.

5. A substantially biologically pure culture according to claim 2, which has no flagellation, requires nicotinic acid or nicotinamide for growth, produces hydrogen sulfide from cysteine, reduces nitrate to nitrite, does not produce acid from sucrose, arabinose, raffinose or sorbitol, produces acid from salicin, cellobiose and glycerol and cannot utilize tartrate as a sole carbon source.

6. A substantially biologically pure culture according to claim 3, which has no flagellation, requires nicotinic acid or nicotinamide for growth, produces hydrogen sulfide from cysteine, reduces nitrate to nitrite, can decarboxylate glutamic acid, does not produce acid from arabinose, mannitol, lactose or sorbitol, produces acid from silicin and cellobiose and cannot use tartrate as a sole carbon source.

7. A substantially biologically pure culture according to claim 1, which is motile by way of mono-lateral flagellum, can grow at a temperature higher than 36° C., exhibits abundant growth on bouillon agar medai, shows mucoid growth, reduces nitrate to nitrite, produces acid from salicin, xylose, melibiose and mannose and can utilize lactate as a sole carbon source.

* * * * *